United States Patent [19]

Onishi et al.

[11] Patent Number: 4,947,001
[45] Date of Patent: Aug. 7, 1990

[54] PROCESS FOR PRODUCING HALOGENATED SULFONE

[75] Inventors: Takashi Onishi; Toshiki Mori; Shigeaki Suzuki, all of Kurashiki; Michio Takigawa, Takatsuki; Kazuo Yamamoto, Kurashiki, all of Japan

[73] Assignee: Kuraray Company, Ltd., Kurashiki, Japan

[21] Appl. No.: 364,154

[22] Filed: Jun. 12, 1989

[30] Foreign Application Priority Data

Jun. 27, 1988 [JP] Japan .................................. 63-160465

[51] Int. Cl.$^5$ ........................................... C07C 149/00
[52] U.S. Cl. ........................................ 568/28; 568/32
[58] Field of Search ................................ 568/28, 32

[56] References Cited

FOREIGN PATENT DOCUMENTS 187259  7/1986  European Pat. Off. .............. 568/32

OTHER PUBLICATIONS

Manchand et al, Helvetica Chimica Acta, vol. 59, pp. 387–396, 1976.
Olson et al, J. Org. Chem., vol. 41, pp. 3287–3293, 1976.

*Primary Examiner*—Anton H. Sutto
*Assistant Examiner*—Deborah D. Carr
*Attorney, Agent, or Firm*—Oblon, Spivak, McClelland, Maier & Neustadt

[57] ABSTRACT

The present invention provides a process for preparing halogenated sulfones by reacting a halogenating agent with a salt of a hydroxysulfone. The halogenated sulfones are useful as an intermediate for vitamin A or its carboxylic acid esters employed as medicines or feed additives.

11 Claims, No Drawings

PROCESS FOR PRODUCING HALOGENATED SULFONE

BACKGROUND OF THE INVENTION

1. Field of the Invention

This invention relates to a process for producing halogenated sulfones of the general formula (I)

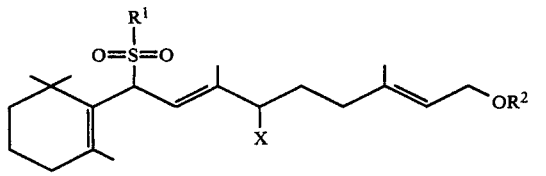

wherein $R^1$ represents a phenyl group which may be substittued, $R^2$ represents a lower acyl group, and X represents a halogen atom.

The halogenated sulfones of the general formula (I) provided according to the invention are useful, as will be described hereinafter, as an intermediate for the preparation of vitamin A and its carboxylic acid esters typical of which are the acetate or palmitate. Vitamin A and its carboxylic acid esters are used as medicines and feed additives.

2. Description of the Related Art

As is described, for excample, in European Patent Publication No. 0 187 259, it is known that halogenated sulfones are prepared by treating hydroxysulfones with a halogenating agent and that the starting hydroxysulfones are prepared by reaction between sulfones and unsaturated aldehydes in the presence of bases.

SUMAMRY OF THE INVENTION

An object of the invention is to provide a process for producing a halogenated sulfone of the general formula (I), which is useful as an intermediate for the preparation of vitamin A and its carboxylic acid esters such as the acetate and palmitate, more easily and more simply than any hitherto known processes.

According to the present invention, the above object can be readily achieved by a process which comprises reacting a halogenating agent with a salt of a hydroxysulfone of the general formula (II)

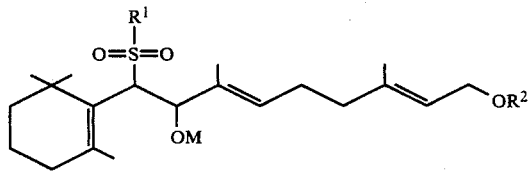

wherein $R^1$ and $R^2$ have, respectively, the same meanings as defined before, and M represents Li or MgY where Y represents a halogen atom.

The hydroxysulfone salt of the general formula (II) can be readily obtained by anionizing a sulfone of the general formula (III)

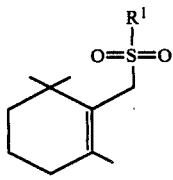

wherein $R^1$ has the same meanings as defined before, with an organic lithium or magnesium reagent and reacting the thus anionized sulfone with an unsaturated aldehyde of the general formula (IV)

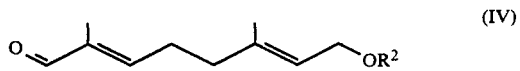

wherein $R^2$ has the same meaning as defined above. This is very important for the industrial-scale production of the halogenated sulfones of the general formula (I) which are useful as an intermediate for the preparation of vitamin A and its carboxylic acid esters such as the acetate and palmitate. More particularly, halogenated sulfones which are useful as an intermediate for the preparation of vitamin A and its carboxylic acid esters such as the acetate and palmitate have been hitherto prepared by initially preparing and isolating a hydroxysulfone according to the process of European Patent Publication No. 0 187 259 and subsequently reacting a halogenating agent with the hydroxysulfone. For the preparation of the intended halogenated sulfone, there are essentially required two independent procedures, i.e. (1) a procedure including a preparation step and an isolation . purification step of the hydroxysulfone and (2) a procedure including a preparation step and an isolation purification step of the halogenated sulfone. In the practice of the invention, however, the halogenated sulfone can be prepared and isolated by a so-called one-pot reaction, not through hydroxysulfone. Thus, the process of the invention is simpler in the procedure of preparing the halogenated sulfone of the general formula (I) than the known process.

DESCRIPTION OF THE PREFERRED EMBODIMENTS $R^1$, $R^2$, M and X in the aforesaid general formulae are described in more detail. $R^1$ represents a phenyl group which may be substituted. Examples of the substituent include a lower alkyl group such as methyl, ethyl, i-propyl, n-propyl, i-butyl, n-butyl or the like, a halogen atom such as chlorine, bromine, iodine or the like, and a lower alkoxy group such as methoxy, ethoxy, i-propoxy, n-propoxy, i-butoxy, n-butoxy or the like. The substituent may be at any of the ortho, meta and para positions and may be one or plural in number. $R^2$ represents a lower acyl group such as formyl, acetyl, propionyl or the like. M represents a lithium atom or MgY wherein Mg is a magnesium atom and Y represents a chlorine, bromine or iodine atom. X represents a halogen atom such as chlorine, bromine and iodine.

When a halogenating agent is acted on the Li or Mg salt of a hyroxysulfone represented by the general formula (II), the halogenated sulfone of the general formula (I) can be obtained. The halogenating agent is, for example, thionyl chloride, thionyl bromide, phosphorus trichloride, phosphorus tribromide or the like. The amount of the halogenating agent is preferably about 1 to 3 equivalents to the Li or Mg salt of hydroxysulfone of the general formula (II). This reaction is favorbly carried out in an organic solvent in the presence of a tertiary amine. The organic solvents are preferably linear or cyclic ethers such as diethyl ether, di-i-propyl ether, di-n-butyl ether, tetrahydrofuran or the like, or mixed solvents of these ethers with aromatic or aliphatic hydrocarbons such as benzene, toluene, xylene, hexane, heptane and the like.

The amount of the organic solvent is preferably such that the concentration of the Li or Mg salt of hydroxysulfone of the general formula (II) is from about 0.1 to 5 mole/liter. The tertiary amine favorably used is, for example, pyridine, triethylamine or the like. These tertiary amines are preferably used in an amount of 0.01 to 50 equivalents to the Li or Mg salts of hydroxysulfone of the general formula (II) and if used in excess, they can also serve as an organic solvent. Preferably, the reaction is carried out within a temperature range of about −30° C. to 30° C.

Next, a procedure of preparing a Li or Mg salt of the hydroxysulfone of the general formula (II) wherein the sulfone of the general formula (III) used as a starting material is rendered anionic or is anionized by the use of an organic lithium or magnesium reagent and is subsequently reacted with the unsaturated aldehyde of the general formula (IV) is described. The organic lithium reagent which is capable of generating an anion at the α-position of the —SO$_2$R$^1$ group of the sulfone of the general formula (III) is, for example, an alkyllithium such as methyllithium, n-butyllithium or the like. On the other hand, the organic magnesium reagent includes, for example, a so-called Grignard reagent such as methylmagnesium chloride, ethylmagensium chloride, methylmagnesium bromide, ethylmagnesium bromide, i-propylmagnesium chloride, n-butylmagnesium chloride or the like.

The amount of the organic lithium or magnesium reagent is 0.5 to 2 molar equivalent to the sulfone of the general formula (III).

The reaction is usually effected within a temperature range of about −100° C. to 70° C. and is favorably carried out in an atmosphere of an inert gas such as helium, nitrogen, argon or the like. Although the reaction time varies depending upon the types of anionizing agent and solvent and the reaction temperature, it is about 3 hours when, for example, the anionizing agent used is n-butyllithium and the reaction is carried out in a tetrahydrofuran solvent at a temperature of about −78° C. to −50° C. Alternatively, the reaction time may be about 6 hours when methylmagnesium chloride is used and the reaction is effected in a tetrahydrofuran solvent at a temperature of about 30° to 40° C. By the reaction between the sulfone of the general formula (III) and the organic lithium or magnesium reagent, an organic lithium or magnesium compound of the general formula (V)

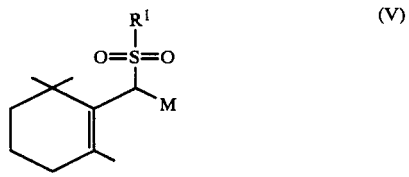

(V)

wherein R$^1$ and M have, respectively, the same meanings as defined before, is formed prior to the reaction with the unsaturated aldehyde of the general formula (IV). This compound may be provided for the reaction with the unsaturated aldehyde of the general formula (IV) as it is without isolation from the reaction system.

The reaction of the organic lithium or magnesium compound of the general formula (V) with the unsaturated aldehyde of the general formula (IV) is usually effected at a temperature of −100° C. to 50° C. and is advantageously carried out in an atmosphere of an inert gas such as helium, nitrogen, argon or the like. In any case, the reaction proceeds very rapidly and the reaction time satisfactorily completes in 2 hours. By the above procedure, the Li or Mg salt of hydroxyfulfone of the general formula (II) can be prepared, and a corresponding halogenated sulfone of the general formula (I) can be prepared according to the afore-described procedure.

The halogenated sulfone of the general formula (I) obtained by the above reactions can be isolated by a usual manner. For instance, the reaction mixture is poured into water, a saturated sodium hydrogen carbonate aqueous solution or diluted sulfuric acid, followed by extraction with benzene, methylene chloride, diethyl ether or ethyl acetate, washing the extract with water and drying with anhydrous sodium sulfate. Subsequently, low boiling matters are distilled off from the extract under reduced pressure and the resultant residue is subjected to silica gel column chromatography, thereby isolating the halogenated sulfone of the general formula (I).

The compound of the general formula (III) is obtained easily in high yield from linalool which is an inexpensive industrial starting material. For instance, a compound of the general formula (III) wherein R$^1$ represents a phenyl group is prepared in the following reaction sequence.

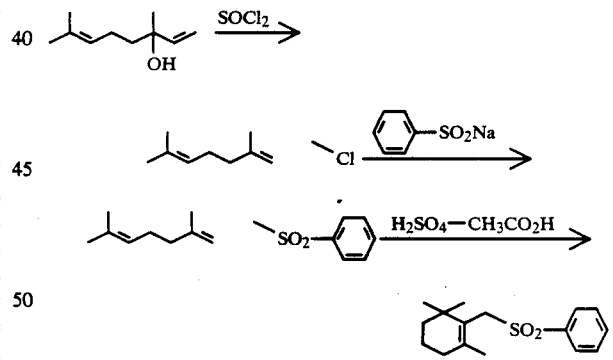

More particularly, thionyl chloride is reacted with linalool to obtain geranyl chloride, followed by reaction between the geranyl chloride and sodium benzenesulfinate to obtain geranyl phenylsulfone. The geranyl phenylsulfone is subjected to ring closure reaction in the present of, for example, a mixed acid of sulfuric acid and acetic acid to obtain β-cyclogeranyl phenylsulfone. During the ring closure reaction, α-cyclogeranyl phenylsulfone which is an isomer of the β-cyclogeranyl phenylsulfone may be by-produced. In this case, the mixture of both compounds is crystallized in a solvent such as hexane to obtain highly pure β-cyclogeranyl phenylsulfone. On the other hand, the α-cyclogeranyl phenylsulfone may be returned to the ring closure system where it is converted into intended β-cyclogeranyl phenylsulfone. The total yield of the β-cyclogeranyl phenylsulfone from linalool is usually about 80%.

The compound of the general formula (IV) is readily prepared by reaction, for example, of selenium dioxide with a lower carboxylic acid ester of geraniol [see Tetrahedron Letters, 281(1973)].

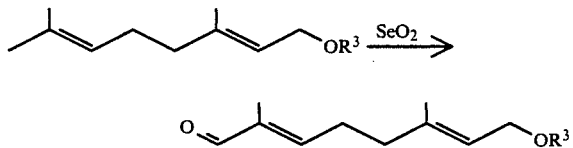

The sulfone of the general formula (I) is readily converted into vitamin A or its acetate in high yield, for example, according to the following reaction sequence.

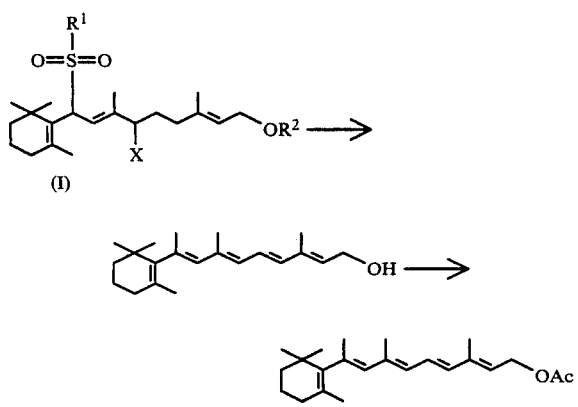

wherein $R^1$, $R^2$ and X have, respectively, the same meanings as defined before.

Vitamin A is obtained by treatment of the halogenated sulfone of the general formula (I) with a base. Examples of the base include potassium alkoxides such as potassium methoxide, potassium ethoxide, potassium t-butoxide and the like, and potassium hyroxide. The amount of the base is preferably about 2 to 20 moles per mole of the halogenated sulfone of the general formula (I). Preferably, the reaction is carried out in an organic solvent. The organic solvents include, for example, hydrocarbons such as hexane, cyclohexane, benzene, toluene and the like. The organic solvent is preferably used in such an amount that the concentration of the halogenated sulfone of the general formula (I) is in the range of about 0.05 to 1 mole/liter. The reaction is favorably effected at a temperature of about 10° to 100° C. After completion of the reaction, the reaction mixture is subjected to filtration, if necessary, to separate the precipitate therefrom to which water, a saturated ammonium chloride aqueous solution or the like is added so as to separate the resultant organic phase. The thus separated organic phase is subjected to purification such as by recrystallization or column chromatography to obtain vitamin A.

If the halogenated sulfone of the general formula (I) is hydrolyzed, a halogenated sulfone of the general formula (I)-1 can be obtained. This compound can be converted into vitamin A under the same conditions as with the halogenated sulfone of the general formula (I).

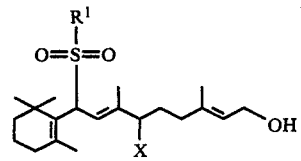

wherein $R^1$ and X have, respectively, the same meanings as defined before.

This hydrolysis reaction can be performed by acting an alkali metal hydroxide on the halogenated sulfone of the general formula (I). Examples of the alkali metal hydroxide include potassium hydroxide, sodium hydroxide, lithium hydroxide and the like. The amount of the alkali metal hydroxide is favorably about 1 to 3 equivalents to the sulfone of the general formula (I). This reaction is preferably effected in a solvent. The solvent used is an alcohol such as methanol, ethanol or the like, or a mixture of the alcohol and water and/or a hydrocarbon such as benzene, toluene or the like. The solvent is preferably used in such an amount that the concentration of the halogenated sulfone of the general formula (I) is in the range of about 0.1 to 10 moles/liter. The reaction is appropriately effected at a temperature of from about $-10°$ C. to 50° C.

The halogenated sulfone of the general formula (I)-1 obtained by the above reaction is separated by a usual manner. For instance, a saturated ammonium chloride aqueous solution, diluted hydrochloric acid or diluted sulfurica acid is added to the reaction mixture to neutralize the remaining alkali metal hydroxide. If necessary, the alcohol used as the solvent may be distilled off and water is added to the resultant residue, followed by extraction with benzene, methylene chloride, diethyl ether, ethyl acetate or the like, washing the resultant extract with water and drying over anhydrous sodium sulfate. Subsequently, low boiling matters are distilled off from the extract and the resultant residue is subjected to silica gel column chromatography to obtain the halogenated sulfone of the general formula (I)-1.

When the thus obtained vitamin A is acetylated, it can be derived into vitamin A acetate. The acetylation reaction is effected by subjecting an acetylation agent to reaction with an organic phase containing the vitamin A separated from the reaction mixture obtained by the formation reaction of vitamin A or with the vitamin A separated and purified from the organic phase. Preferably, this reaction is carried out in an organic solvent in the presence of a tertiary amine. The acetylation agents include, for example, anhydrous acetic acid, acetyl chloride and the like. The amount of the acetylation agent is preferably in the range of from about 1 to 10 equivalents to the vitamin A used. The organic solvents include, for example, hydrocarbons such as benzene, toluene, hexane, heptane and the like, halogenated hydrocarbons such as methylene chloride, 1,2-dichloroethane and the like, ethers such as diethyl ether, diisopropyl ether and the like, and esters such as ethyl acetate, butyl acetate and the like.

These organic solvents are preferably used in such an amount that the concentration of vitamin A is in the range of about 0.1 to 5 moles/liter. The tertiary amine is, for example, treithylamine, pyridine or the like. These tertiary amines are preferably used in an amount of about 0.01 to 10 equivalents to the vitamin A. If the tertiary amine is used in excess, it also serves as an organic solvent. the reaction is conveniently effected at a temperature of about −10° C. to 100° C. After completion of the reaction, the resultant precipitate may be removed from the reaction mixture by filtration, if necessary, after which diluted sulfuric acid, water or a saturated sodium hydrogen carbonate aqueous solution is added to the reaction mixture, followed by separation of the resultant organic phase. When the organic phase is subjected to purification such as by recrystallization or column chromatography, vitamin A acetate can be obtained.

The present invention is described by way of examples, which should not be construed as limiting the invention thereto.

EXAMPLE 1

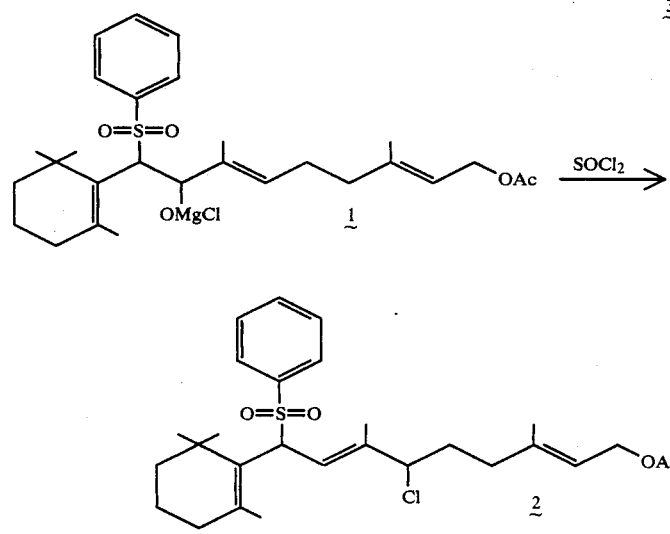

A 50 ml round bottom flask was charged with 2.12 g (3.87 mmols) of a magnesium chloride salt (1) of 1-acetoxy-8-hydroxy-3,7-dimethyl-9-(2,6,6-trimethyl-1-cyclohexen-1-yl)-9-phenylksulfonyl-2,6-nonadiene, 15 ml of toluene, 2.3 ml of tetrahydrofuran and 0.61 g of pyridine, to which 0.63 g of thionyl chloride was added while cooling to −30° C., at which the mixture was agitated for 15 minutes and then at −10° C. to 0° C. for 30 minutes. The reaction mixture was poured into 50 ml of water, followed by extraction with 50 ml of toluene to collect an organic phase. The aqueous phase was again extracted with 50 ml of toluene. These organic phases were combined, followed by washing with a saturated sodium carbonate aqueous solution and then with a saturated sodium carbonate aqueous solution and drying over anhydrous magensium sulfate. The solvent was distilled off from the organic phase and the resultant residue was purified by the column chromatography using silica gel (elute: a mixed solution of hexane and ethyl acetate at a ratio by volume of 5:1) to obtain 1.85 g of a white waxy substance. From the following data of instrumental analyses, the substance was confirmed to be 1-acetoxy-6-chloro-3,7-dimethyl-9-(2,6,6-trimethyl-1-cyclohexene-1-yl)-9-phenylsulfonyl-2,7-nonadiene. The yield was 94%.

NMR $\delta_{(CH_3)_3SiOSi(CH_3)_3}^{CDCl_3}$: 0.72–2.05(m,28H), 4.17–4.57(m,4H), 5.23(t,1H), 5.88(m,1H), 7.35–7.91(m,5H)

IR (film) $\nu$ (cm$^{-1}$): 1745(C=O), 1150(SO$_2$), 685(C$_6$H$_5$).

FD-MS m/e: 506(M$^+$), 507(M$^+$+1), 470(M$^+$−HCl), 365(M$^+$−C$_6$H$_5$SO$_2$).

EXAMPLE 2

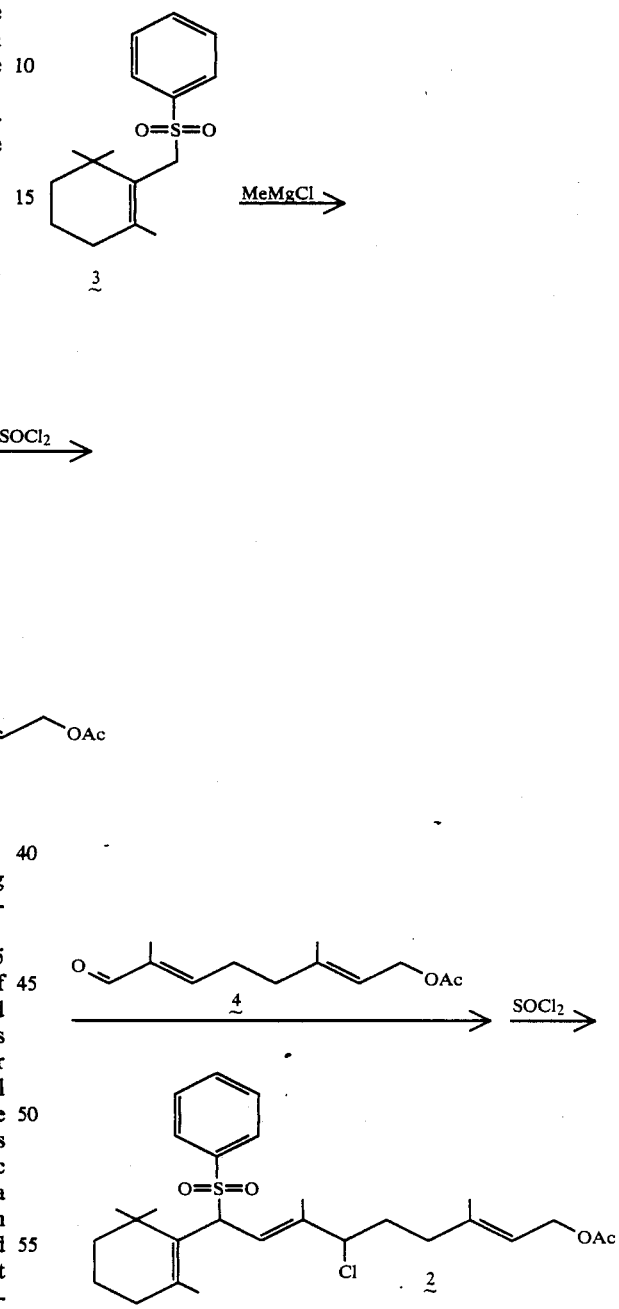

5.40 g (19.4 mmols) of β-cyclogeranyl phenylsulfone (3) and 50 ml of tetrahydrofuran were charged into a 200 ml three-necked flask purged with a nitrogen gas, in which 16.8 ml (18.5 mmols) of a tetrahydrofuran solution of methylmagnesium chloride (1.1 mols/liter) was dropped at an inner temperature of 30° to 40° C. After completion of the dropping, agitation was further continued at an inner temperature of 30° to 40° C. for 6 hours. Subsequently, the reaction solution was cooled down to an inner temperature of −30° to −40° C. and was gradually dropped in a solution of 3.70 g (17.6 mmols) of 8-acetoxy-2,6-dimethyl-2,6-octadien-1-al (4) in 30 ml of toluene while keeping the inner temperature at −30° C. to −40° C. After completion of the dropping, the solution was agitated at the same temperature for further 1 hour.

3.62 g (45.8 mmols) of pyridine was added to the reaction mixture, in which 2.72 g (22.9 mmols) of thionyl chloride was dropped at an inner temperature of −30° to −40° C., followed by agitation at the temperature for 30 minutes. Thereafter, the inner temperature was raised to 0° C., followed by agitation at 0° C. to 10° C. for 30 minutes.

The reaction mixture was poured into 200 ml of water, to which 100 ml of toluene was added for extract in the organic phase. The lower phase was further extracted with 100 ml of toluene. These organic phases were combined together, washed with a saturated sodium carbonate aqueous solution and then with a saturated sodium chloride aqueous solution, and dried over anhydrous magnesium sulfate. The solvent was distilled off from the organic phase under reduced pressure and the resultant residue was purified by column chromatography using silica gel (elute: a mixed solution of hexane and ethyl acetate at a ratio by volume of 5:1), thereby obtaining 7.55 g of a white waxy substance. The yield based on the 8-acetoxy-2,6-dimethyl-2,6-octadien-1-al was 84.6%.

EXAMPLES 3–8

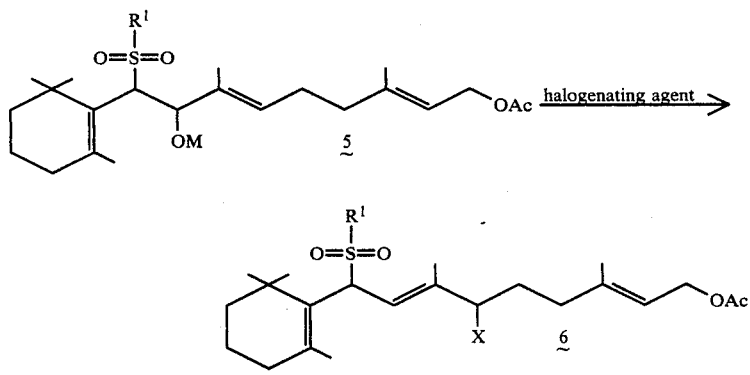

20 ml of a solution of 3.87 mmols of compound 5 in 20 ml of tetrahydrofuran was placed in a 50 ml round bottom flask and was cooled to −30° to −40° C. Thereafter, predetermined amounts of halogenating agents were added to the solution, followed by agitation at the same temperature for 30 minutes and then at 0° to 15° C. for further 2 hours. The reaction mixtures were each treated in the same manner as in Example 1 to separate halogenated sulfones 6. The results are shown in the following table.

| Example | 5 R¹ | M | Halogenating Agent | Halogenating Agent/5 (molar ratio) | 6 X | Yield (%) |
|---|---|---|---|---|---|---|
| 3 | —C₆H₅ | MgCl | SOCl₂ | 3.0 | Cl | 88.3 |
| 4 | " | " | PCl₃ | 2.3 | " | 61.0 |
| 5 | " | " | POCl₃ | 2.3 | " | 47.3 |
| 6 | " | " | PBr₃ | 2.1 | Br | 71.0 |
| 7 | —C₇H₇(P) | " | SOCl₂ | 3.0 | Cl | 82.8 |

| Example | 5 R¹ | M | Halogenating Agent | Halogenating Agent/5 (molar ratio) | 6 X | Yield (%) |
|---|---|---|---|---|---|---|
| 8 | —C₆H₅ | Li | SOCl₂ | 3.0 | " | 85.0 |

Reference 1

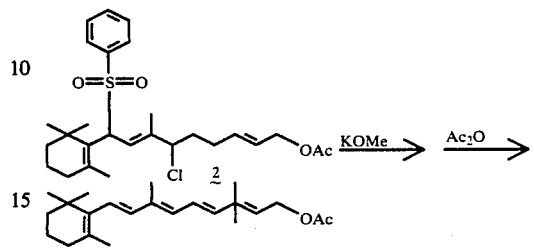

A 50 ml flask purged with an argon gas was charged with 0.4951 g (0.977 mmols) of 1-acetoxy-6-chloro-3,7-dimethyl-9-(2,6,6-trimethyl-1-cyclohexen-1-yl)-9-phenylsulfonyl-2,7-nonadiene(2) and 15 ml of cyclohexane and agitated for a while, to which 0.70 g (10 mmols) of potassium methoxide was added. Followed by agitation at 38° C. for 2 hours. 30 ml of diisopropyl ether and 15 ml of a saturated ammonium chloride aqueous solution were added to the reaction mixture and the resultant organic phase was separated. The aqueous phase was extracted with 20 ml of diisopropyl ether. The organic phases were combined together, washed with a saturated ammonium chloride solution and dried over anhydrous magnesium sulfate. The organic solvent was distilled off from the organic phase and the resultant residue was placed in a 100 ml flask, purged with an argon gas, along with 4 ml of a hexane solution containing 0.05 wt % of 2,6-di-t-butyl-4-methylphenol and 1.1 ml of triethylamine, 0.68 ml of acetic anhydride was added to the mixture under ice-cooling conditions, followed by agitation at room temperature for 1 day. 50 ml of hexane and 10 ml of a saturated sodium hydrogen carbonate aqueous solution were added to the reaction mixture and agitated for a time, after which the hexane phase was separated. This hexane phase was washed with a saturated sodium hydrogen carbonate aqueous solution and dried over anhydrous magnesium sulfate. The hexane was removed by distillation from the hexane phase to obtain 0.3462 g of a red oily substance. This oily substance was subjected to FD-MS analysis, revealing a peak at m/e=328. From this, the oily substance was confirmed to be mainly composed of vitamin A acetate. Subsequently, the formed vitamin A acetate was quantitatively determined using a high speed liquid chromatography wherein methyl stearate was employed as an internal standard. As a result, it was found that the yield of the vitamin A acetate was 70% based on the 1-acetoxy-6-chloro-3,7-dimethyl-9-(2,6,6-trimethyl-1-cyclohexen-1-yl)-9-phenylsulfonyl-2,7-nonadiene(2).

Reference 2

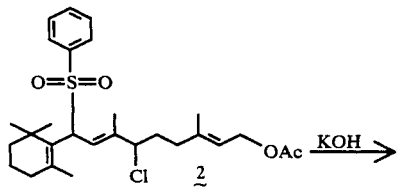

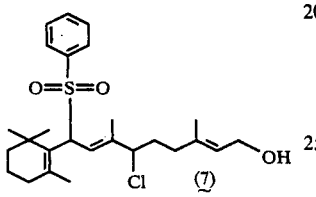

A 10 ml round bottom flask was charged with 0.0226 g (0.342 mmols) of potassium hydroxide and 1 ml of methanol, followed by agitation at room temperature to prepare a methanol solution of potassium hydroxide. To the solution was added a solution of 0.0373 g (0.0736 mmols) of 1-acetoxy-6-chloro-3,7-dimethyl-9-(2,6,6-trimethyl-1-cyclohexen-1-yl)-9-phenylsulfonyl-2,7-nonadiene (2) dissolved in a mixed solvent of 2 ml of methanol and 0.2 ml of benzene, followed by agitation on an iced water bath for 30 minutes. A saturated ammonium chloride aqueous solution was added to the reaction mixture, from which the solvent was removed by distillation, followed by addition of water to the resultant residue and extraction with diethyl ether. The extract was washed with a saturated ammonium chloride aqueous solution and dried over anhydrous magnesium sulfate. The solvent was distilled off from the extract to obtain 0.0297 g of a yellow oily substance. The following data of instrumental analyses revealed that the substance was 6-chloro-1-hydroxy-3,7-dimethyl-9-(2,6,6-trimethyl-1-cyclohexen-1-yl)-9-phenylsulfonyl-2,7-nonadiene (7). The yield was 87%.

NMR $\delta_{(CH_3)_3SiOSi(CH_3)_3}^{CDCl_3}$: 0.75–2.20(m,26H), 4.06 (d,2H), 4.21–4.55(m,2H), 5.30(t,1H), 5.91(m,1H), 7.36–7.90(m,5H).

IR (film) $\nu$ (cm$^{-1}$): 3300 (OH), 1745(C=O), 1150(SO$_2$), 685(C$_6$H$_5$).

FD-MS m/e: 465(M$^+$+1), 428(M$^+$−HCl), 323(M$^+$−C$_6$H$_5$SO$_2$).

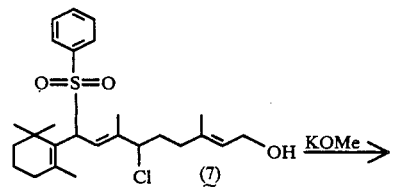

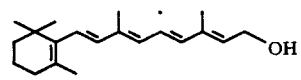

A 10 ml flask which had been purged with an argon gas was charged with 0.0232 g (0.050 mmols) of 6-chloro-1-hydroxy-3,7-dimethyl-9-(2,6,6-trimethyl-1-cyclohexen-1-yl)-9-phenylsulfonyl-2,7-nonadiene (7) and 5 ml of cyclohexane, to which 0.0352 g (0.50 mmols) of potassium methoxide was added, followed by agitation at 35° C. for 2 hours. The reaction mixture was added to a mixed solution of 20 ml of diisopropyl ether and 10 ml of a saturated ammonium chloride solution. The resultant organic phase was separated and dried over anhydrous magnesium sulfate and concentrated to about 1 ml. The concentrate was subjected to FD-MS analysis to detect a peak at m/e=286. From this, the concentrate was confirmed to contain vitamin A.

Reference 3

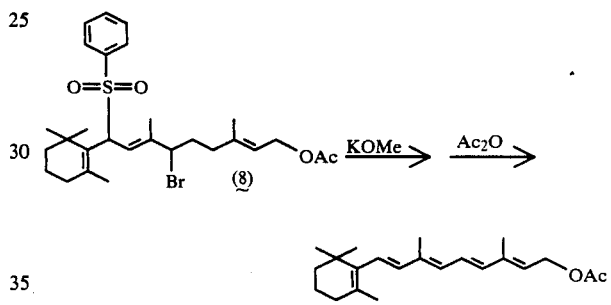

The reaction and separation procedures of Reference 1 were repeated except that there was used, instead of 0.4951 g (0.977 mmols) of 1-acetoxy-6-chloro-3,7-dimethyl-9-(2,6,6-trimethyl-1-cyclohexen-1-yl)-9-phenylsulfonyl-2,7-nonadiene, 0.5538 g (1.01 mmols) of 1-acetoxy-6-bromo-3,7-dimethyl-9-(2,6,6-trimethyl-1-cyclohexene-1-yl)-9-phenylsulfonyl-2,7-nonadiene (8) and that there was used a mixture of 10 ml of cyclohexane and 5 ml of toluene instead of 15 ml of cyclohexane, thereby obtaining 0.3195 g of a red oily substance. This oily substance was subjected to FD-MS analysis to detect a peak at m/e=328. This revealed that the main component of the oily substance was vitamin A acetate. Subsequently, the vitamin A acetate was quantitatively determined by high speed liquid chromatography in the same manner as in Reference 1 with the result that the yield of the vitamin A acetate was 70% based on the 1-acetoxy-6-bromo-3,7-dimethyl-9-(2,6,6-trimethyl-1-cyclohexene-1-yl)-9-phenylsulfonyl-2,7-nonadiene (8).

Reference 4

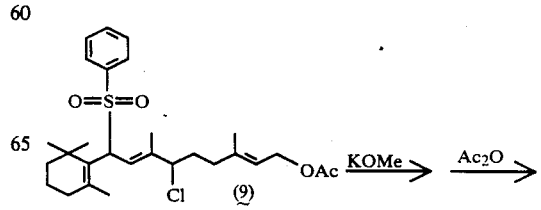

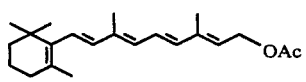

The reaction and separation procedures of Reference 3 were repeated except that there was used, instead of 0.5538 g (1.01 mmols) of 1-acetoxy-6-bromo-3,7-dimethyl-9-(2,6,6-trimethyl-1-cyclohexene-1-yl)-9-phenylsulfonyl-2,7-nonadiene (8), 0.5127 g (0.985 mmols) of 1-acetoxy-6-chloro-3,7-dimethyl-9-(2,6,6-trimethyl-1-cyclohexen-1-yl)-9-(p-tolyl)sulfonyl-2,7-nonadiene (9), thereby obtaining 0.3325 g of a red oily substance. This oily substance was subjected to FD-MS analysis to detect a peak at m/e=328. From this, it was confirmed that the main component of the oily substance was vitamin A acetate. Thereafter, the vitamin A acetate was quantitatively determined by high speed liquid chromatography in the same manner as in Reference 1, so that the yield was 68% based on the 1-acetoxy-6-chloro-3,7-dimethyl-9-(2,6,6-trimethyl-1-cyclohexen-1-yl)-9-(p-tolyl)sulfonyl-2,7-nonadiene (9).

What is claimed is:

1. A process for preparing a halogenated sulfone of the general formula (I)

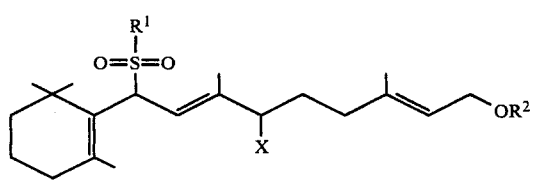

wherein $R^1$ represents a phenyl group which may be substituted with at least one member of the group consisting of lower alkyl, halogen and lower alkoxy, $R^2$ represents a lower acyl group, and X represents a halogen atom, characterized by reacting a halogenating agent with a salt of a hydroxysulfone of the following general formula (II)

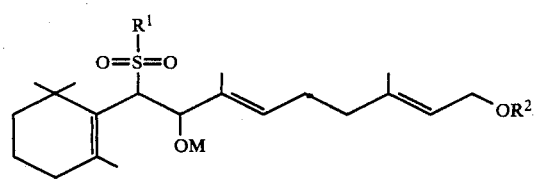

wherein $R^1$ and $R^2$ have the same meanings as defined above and M represents Li or MgY where Y represents a halogen atom, in the presence of an etherial solvent.

2. A process according to claim 1, wherein said halogenating agent is a halogen compound selected from the group consisting of thionyl chloride, thionyl bromide, phosphorus trichloride and phosphorus tribromide.

3. A process according to claim 1, wherein the reaction is effected in a linear or cyclic ether solvent or in a mixed solvent of the ether and an aromatic or aliphatic hydrocarbon.

4. A process according to claim 1, wherein the reaction is effected at a temperature of from —30° C. to 30° C.

5. A process according to claim 1, wherein the reaction is effected in coexistence of a tertiary amine.

6. A process for preparing a halogenated sulfone of the general formula (I)

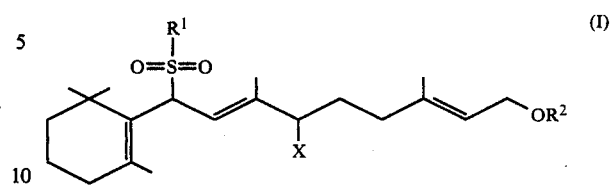

wherein, $R^1$ represents a phenyl group which may be substituted with at least one member of the group consisting of lower alkyl, halogen and lower alkoxy, $R^2$ represents a lower acyl group, and X represents a halogen atom, characterized by anionizing a sulfone of the general formula (III)

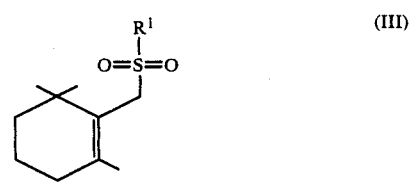

wherein $R^1$ has the same meaning as defined above, with an organic lithium or magnesium reagent in the presence of an etherial solvent, reacting the resulting product with an unsaturated aldehyde of the general formula (IV)

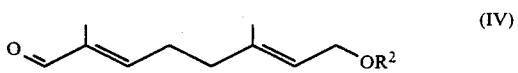

wherein $R^2$ has the same meaning as defined above, thereby obtaining a salt of a hydroxysulfone of the general formula (II)

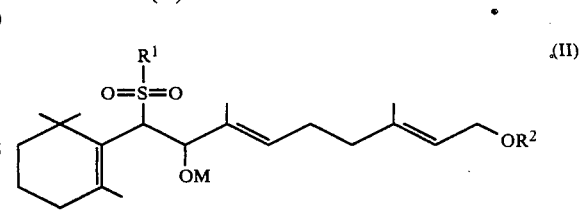

wherein $R^1$ and $R^2$ have the same meanings as defined above and M represents Li or MgY where Y represents a halogen atom, and reacting a halogenating agent with the salt of the hydroxysulfone obtained above, in the presence of an etherial solvent.

7. A process according to claim 6, wherein the sulfone of the general formula (III) and the organic lithium or magnesium reagent are reacted in the presence of a etherial solvent at a temperature between —100° C. and 40° C. to form a compound of the general formula (V)

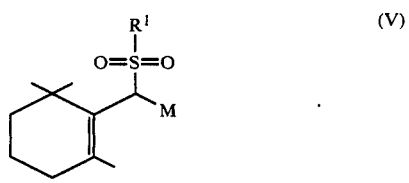

wherein $R^1$ has the same meaning as defined above and M represents Li or Mg Y where Y is a halogen atom, said compound of the general formula (V) being used for reaction with the unsaturated aldehyde of the general formula (IV).

8. The process of claim 3 wherein said ether is diethyl ether, di-i-propyl ether, di-n-butyl ether or tetrahydrofuran and said hydrocarbon is benzene, toluene, xylene, hexane or heptane.

9. The process of claim 8 wherein the halogenation is carried out in the presence of an amine base.

10. The process of claim 6 wherein said etherial solvent is diethyl ether, di-i-propyl ether, di-n-butyl ether or tetrahydrofuran.

11. The process of claim 6 wherein the halogenation is carried out in the presence of an amine base.

* * * * *